United States Patent [19]

Metzger et al.

[11] 3,981,714
[45] Sept. 21, 1976

[54] CYCLIC N-THIADIAZOLYL-(2)-CARBOXYLIC ACID COMPOUNDS AND HERBICIDAL COMPOSITIONS

[75] Inventors: Carl Metzger, Dormagen; Ludwig Eue; Robert Rudolf Schmidt, both of Cologne, all of Germany

[73] Assignee: Bayer Aktiengesellschaft, Leverkusen, Germany

[22] Filed: Feb. 24, 1975

[21] Appl. No.: 552,506

[30] Foreign Application Priority Data
Mar. 9, 1974 Germany............................ 2411288
Mar. 28, 1974 Germany............................ 2415056

[52] U.S. Cl. .............................. 71/90; 260/293.68; 260/306.8 D
[51] Int. Cl.² ...................................... C07D 417/04
[58] Field of Search ............... 260/306.8 D, 293.68, 260/293.57; 71/90

[56] References Cited
UNITED STATES PATENTS
3,657,264  4/1972  Rucker et al. ............... 260/306.8 D

*Primary Examiner*—Nicholas S. Rizzo
*Assistant Examiner*—Mary C. Vaughn
*Attorney, Agent, or Firm*—Burgess, Dinklage & Sprung

[57] ABSTRACT

Novel cyclic N-thiadiazolyl-(2)-carboxylic acid amide compounds of the formula:

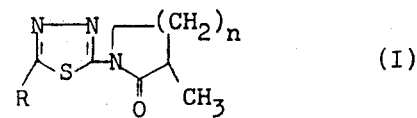

wherein
R is alkyl, haloalkyl, alkylthio, alkylsulfonyl or alkoxy, and
n is 1 or 2, display strong herbicidal properties.

14 Claims, No Drawings

CYCLIC N-THIADIAZOLYL-(2)-CARBOXYLIC ACID COMPOUNDS AND HERBICIDAL COMPOSITIONS

The present invention relates to certain novel cyclic N-thiadiazolyl-(2)-carboxylic acid amide compounds, and to herbicidal compositions and uses thereof.

It is known that some derivatives of certain cyclic carboxylic acid amides display herbicidal properties. Thus, for example, 1-(3,4-dichlorophenyl)-3-methyl-2-pyrrolidone and 1-(3, 4-dichlorophenyl)-3-methyl-2-piperidone can be employed to combat weeds (see Belgian Patent Specification No. 662,762). However, the activity of these compounds is not always entirely satisfactory, especially if low amounts and low concentrations are used.

The present invention provides, as new compounds, the cyclic N-thiadiazolyl-(2)-carboxylic acid amides of the general formula:

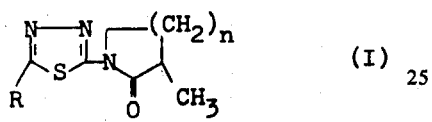

wherein
R is alkyl, haloalkyl, alkylthio, alkylsulfonyl or alkoxy, and
$n$ is 1 or 2.

The compounds of this invention have been found to display strong herbicidal properties.

Preferably R is straight-chain or branched alkyl of from 1 to 5 carbon atoms, haloalkyl of from 1 to 2 carbon atoms and 2 to 5 halogen atoms (especially trifluoromethyl), or straight-chain or branched alkylthio, alkoxy or alkylsulfonyl, each of from 1 to 4 carbon atoms.

Surprisingly, the cyclic N-thiadiazolyl-(2)-carboxylic acid amides according to the invention show a substantially higher herbicidal activity than the compounds 1-(3,4-dichlorophenyl)-3-methyl-pyrrolidone and 1-(3,4-dichlorophenyl)-3-methyl-2-piperidone known from the state of the art. In addition, the compounds according to the invention are substantially more suitable than the aforesaid prior-art compounds, for combating certain weeds such as camomile (Matricaria) or wild carrot (Daucus). The compounds according to the invention thus represent a valuable enrichment of the art.

The invention also provides a process for the preparation of a cyclic N-thiadiazolyl-(2)-carboxylic acid amide of the formula (I), in which an N-thiadiazolyl-(2)-ω-halogenocarboxylic acid amide of the general formula:

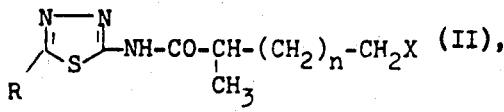

wherein
R and $n$ have the above-mentioned meanings, and
X is halogen, preferably chlorine, bromine or iodine, is reacted with an acid-binding agent, if appropriate in the presence of a diluent.

If α-methyl-γ-chlorobutyric acid N-(5-tert.-butyl-1,3,4-thiadiazol-2-yl)-amide is used as the starting material, the course of the reaction can be represented by the following equation:

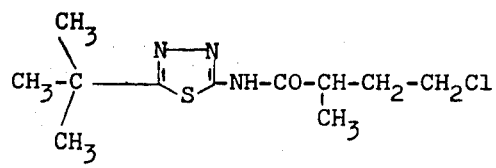

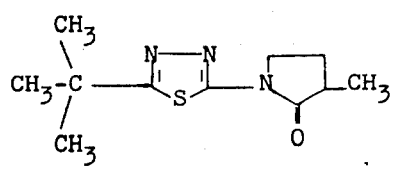

The following may be mentioned as examples of the N-thiadiazolyl-(2)-ω-halogenocarboxylic acid amides of the formula (II) which can be used according to the invention: α-methyl-γ-chlorobutyric acid N-(5-tert.-butyl-1,3,4-thiadiazol-2-yl)-amide, α-methyl-δ-iodovaleric acid N-(5-tert.-butyl-1,3,4-thiadiazol-2-yl)-amide, α-methyl-γ-chlorobutyric acid N-(5-methyl-1,3,4-thiadiazol-2-yl)-amide α-methyl-γ-chlorobutyric acid N-(5-ethyl-1,3, 4-thiadiazol-2-yl)-amide, α-methyl-γ-chlorobutyric acid N-(5-n-propyl-1,3,4-thiadiazol-2-yl)-amide, α-methyl-γ-chlorobutyric acid N-(5-isopropyl-1,3,4-thiadiazol-2-yl)-amide, α-methyl-γ-chlorobutyric acid N-(5-trifluoromethyl-1,3,4-thiadiazol-2-yl)-amide, α-methyl-γ-chlorobutyric acid N-(5-methylthio-1,3,4-thiadiazol-2-yl)-amide, α-methyl-γ-chlorobutyric acid N-(5-ethylthio-1,3,4-thiadiazol-2-yl)-amide, α-methyl-γ-chlorobutyric acid N-(5-methylsulfonyl-1,3,4-thiadiazol-2-yl)-amide, α-methyl-γ-chlorobutyric acid N-(5-ethylsulfonyl-1,3,4-thiadiazol-2-yl)-amide, α-methyl-γ-chlotobutyric acid N-(5-methoxy-1,3,4-thiadiazol-2-yl)-amide, α-methyl-δ-chlorobaleric acid N-(5-n-butyl-1,3,4-thiadiazol-2-yl)-amide, α-methyl-δ-chlorovaleric acid N-(5-isobutyl-1,3,4-thiadiazol-2-yl)-amide, α-methyl-δ-chlorovaleric acid N-(5-methyl-1,3,4-thiadiazol-2-yl)-amide, α-methyl-δ-bromovaleric acid N-(5-ethyl-1,3,4-thiadiazol-2-yl)-amide, α-methyl-δ-bromovaleric acid N-(5-trifluoromethyl-1,3,4-thiadiazol-2-yl)-amide, α-methyl-δ-bromovaleric acid N-(5-methylthio-1,3,4-thiadiazol-2-yl)-amide, α-methyl-δ-iodovaleric acid N-(5-ethylthio-1,3,4-thiadiazol-2-yl)-amide, α-methyl-δ-iodovaleric acid N-(5-ethylsulfonyl-1,3,4-thiadiazol-2-yl)-amide, α-methyl-δ-iodovaleric acid N-(5-methylsulfonyl-1,3,4-thiadiazol-2-yl)-amide and α-methyl-δ-iodovaleric acid N-(5-methoxy-1,3,4-thiadiazol-2-yl)-amide.

The N-thiadiazolyl-(2)-ω-halogenocarboxylic acid amides of the formula (II) used as starting materials have not previously been described in the literature. However, they can be prepared in a simple manner in accordance with processes described in the literature (see Bulletin de la Societe Chimique de France 1967 (3), 1010 – 1012). Thus, for example, the N-thiadiazolyl-(2)-ω-halogenocarboxylic acid amides of the formula (II) may be obtained by reacting 5-amino-1,3,4-thiadiazoles of the general formula:

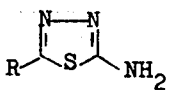

(III), wherein

R has the above-mentioned meaning, with α-methyl-ω-halogeno-carboxylic acid halides of the general formula:

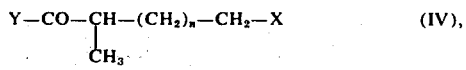

(IV), wherein

X and n have the above-mentioned meanings, and
Y is chlorine or bromine, in the presence of an acid-binding agent, for example triethylamine, and in the presence of a solvent, for example ethyl acetate, at temperatures between 0°C and 50°C, preferably between 10°C and 30°C. The compounds of the formula (II) are isolated by first filtering off the salts produced in the reaction, then concentrating the filtrate and finally, if appropriate, recrystallizing the residue. The compounds of the formulas (III) and (IV) used as starting materials are known or can be manufactured according to customary processes.

Preferred diluents (which term includes solvents) for carrying out the reaction according to the invention for the preparation of the compounds of the formula (I) are water, lower alcohols, such as methanol and ethanol, and mixtures of these alcohols with water, in any desired ratios.

All customary acid acceptors can be used as the acid-binding agents. Preferred acid acceptors are alkali metal carbonates, such as potassium carbonate and sodium carbonate, alkaline earth metal carbonates, such as barium carbonate and magnesium carbonate, alkaline earth metal hydroxides, such as barium hydroxide and magnesium hydroxide, and tertiary organic bases, such as triethylamine or pyridine. Alkali metal hydroxides, such as sodium hydroxide and potassium hydroxide, should be mentioned as being particularly suitable.

The reaction temperatures can be varied within a fairly wide range. In general, the reaction is carried out at temperatures between 40°C and 130°C, preferably between 50°C and 120°C.

In general, the reaction is carried out at normal pressure.

In carrying out the process according to the invention for the preparation of the compounds of the formula (I), preferably 1 mole of an acid acceptor is employed per mole of N-thiadiazolyl-(2)-ω-halogenocarboxylic acid amide of the formula (II). However, it is also possible to use an excess of acid acceptor. This, however, does not significantly improve the yield.

The reaction products of the formula (I) are isolated by pouring the reaction mixture, after completion of the reaction, into water, filtering off the products which are hereupon obtained in a crystalline form, and optionally recrystallizing them in order to achieve further purification.

The following should be mentioned as examples of the cyclic N-thiadiazolyl(2)-carboxylic acid amides according to the invention: 1-[5-tert.-butyl-1,3,4-thiadiazolyl-(2)]-3-methyl-2-pyrrolidone, 1-[5-tert.-butyl-1,3,4-thiadiazolyl-(2)]-3-methyl-2-piperidone, 1-[5-methyl-1,3,4-thiadiazolyl-(2)]-3-methyl-2-pyrrolidone, 1-[5-ethyl-1,3,4-thiadiazolyl-(2)]-3-methyl-2-pyrrolidone, 1-[5-n-propyl-1,3,4-thiadiazolyl-(2)]-3-methyl-2-pyrrolidone, 1-[5-isopropyl-1,3,4-thiadiazolyl-(2)]-3-methyl-2-pyrrolidone, 1-[5-trifluoromethyl-1,3,4-thiadiazolyl-(2)]-3-methyl-2-pyrrolidone, 1-[5-methylthio-1,3,4-thiadiazolyl-(2)]-3-methyl-2-pyrrolidone, 1-[5-ethylthio-1,3,4-thiadiazolyl-(2)]-3-methyl-2-pyrrolidone, 1-[5-ethylsulfonyl-1,3,4-thiadiazolyl-(2)]-3-methyl-2-pyrrolidone, 1-[5-methylsulfonyl-1,3,4-thiadiazolyl-(2)]-3-methyl-2-pyrrolidone, 1-[5-methoxy-1,3,4-thiadiazolyl-(2)]-3-methyl-2-pyrrolidone, 1-[5-n-butyl-1,3,4-thiadiazolyl-(2)]-3-methyl-2-piperidone, 1-[5-iso-butyl-1,3,4-thiadiazolyl-(2)]-3-methyl-2-piperidone, 1-[(5-methyl-1,3,4-thiadiazolyl-(2)]-3-methyl-2-piperidone, 1-[(5-ethyl-1,3,4-thiadiazolyl-(2)]-3-methyl-2-piperidone, 1-[(5-trifluoromethyl-1,3,4-thiadiazolyl-(2)]-3-methyl-2-piperidone, 1-[(5-methylthio-1,3,4-thiadiazolyl-(2)]-3-methyl-2-piperidone, 1-[(5-ethylthio-1,3,4-thiadiazolyl-(2)]-3-methyl-2-piperidone, 1-[(5-ethylsulfonyl-1,3,4-thiadiazolyl-(2)]-3-methyl-2-piperidone, 1-[(5-methylsulfonyl-1,3,4-thiadiazolyl-(2)]-3-methyl-2-piperidone and 1-[(5-methoxy-1,3,4-thiadiazolyl-(2)]-3-methyl-2-piperidone.

The following examples are given for the purpose of illustrating the preparation of the compounds used in the present invention:

EXAMPLE 1

Preparation of
1-[5-tert.-butyl-1,3,4-thiadiazolyl(2)]-3-methyl-2-pyrrolidone

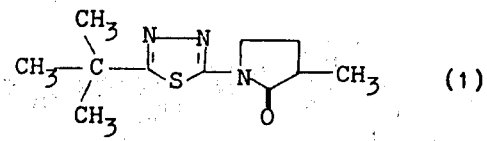

(1)

55.1 g (0.2 mole) of α-methyl-γ-chlorobutyric acid N-(5-tert.-butyl-1,3,4-thiadiazol-2-yl)-amide were added to a solution of 11.2 g (0.2 mole) of powdered potassium hydroxide in a mixture of 32 ml of water and 80 ml of ethanol. The reaction mixture was heated under reflux for 10 minutes and after subsequent cooling was poured into 280 ml of water. The solid residue which hereupon separated out was filtered off, dried and recrystallized from a mixture of petroleum ether and ethyl acetate (in the ratio 4:1).

This gave 31.4 g (65% of theory) of 1-[5-tert.-butyl-1,3,4-thiadiazolyl-(2)]-3-methyl-2-pyrrolidone of melting point 113°–114°C.

EXAMPLE 2

Preparation of
1-[5-tert.-butyl-1,3,4-thiadiazolyl(2)]-3-methyl-2-piperidone

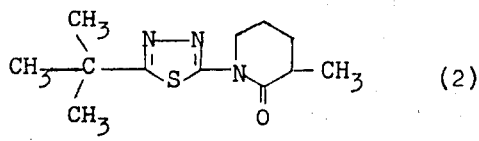

A mixture of 34.0 g (0.089 mole) of α-methyl- -iodo- valeric acid N-(5-tert.-butyl-1,3,4-thiadiazol-2-yl)-amide, 4.9 g (0.089 mole) of powdered potassium hydroxide, 14.5 ml of water and 36 ml of ethanol was heated for 10 minutes under reflux. After cooling, the reaction mixture was poured into 90 ml of water. This solution was stirred until a crystalline precipitate had separated out. The crystalline product was filtered off, dried and recrystallized from ligroin.

This gave 14.0 g (61.5% of theory) of 1-[5-tert.-butyl-1,3,4-thiadiazolyl-(2)]-3-methyl-2-piperidone of melting point 90°–91°C.

The active compounds listed in Table 1 which follows were prepared analogously:

Table 1

$$R-\underset{S}{\overset{N-N}{\underset{}{\bigvee}}}-N\underset{O}{\overset{(CH_2)_n}{\bigvee}}CH_3 \quad (1)$$

| Example No. | R | n | Melting point [°C] |
|---|---|---|---|
| 3 | $CH_3$ | 1 | 137 – 138 |
| 4 | $C_2H_5$ | 1 | 95 – 96 |
| 5 | $n-C_3H_7$ | 1 | 125 – 126 |
| 6 | $i-C_3H_7$ | 1 | 113 |
| 7 | $CF_3$ | 1 | 118 – 119 |
| 8 | $CH_3S$ | 1 | 86 |
| 9 | $C_2H_5S$ | 1 | 50 |
| 10 | $C_2H_5SO_2$ | 1 | 90 |
| 11 | $CH_3SO_2$ | 1 | 110 |
| 12 | $CH_3O$ | 1 | 79 – 80 |

The starting materials of the formula (II) were prepared as follows:

EXAMPLE I

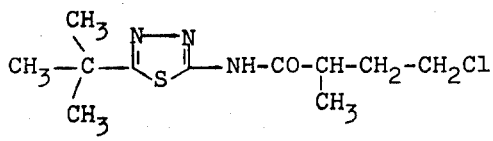

46.5 g (0.3 mole) of α-methyl-γ-chlorobutyric acid chloride were added dropwise over the course of 30 minutes to a mixture of 47.1 g (0.3 mole) of 5-amino-2-tert.-butyl-1,3,4-thiadiazol and 30.3 g (0.3 mole) of triethylamine in 750 ml of anhydrous ethyl acetate at 20°C. After stirring for 4 hours at 25°C, the triethylammonium chloride formed was filtered off. The filtrate was freed from the solvent and the crystalline residue which remained was recrystallized from 75% strength aqueous methanol. This gave 66.6 g (81% of theory) of α-methyl-γ-chlorobutyric acid N-(5-tert.-butyl-1,3,4-thiadiazol-2-yl)-amide of melting point 124.5°–126°C.

EXAMPLE II

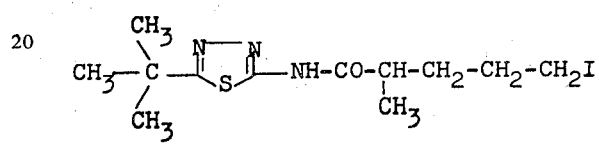

31.4 g (0.2 mole) of 5-amino-2-tert.-butyl-1,3,4-thiadiazole were suspended in a mixture of 250 ml of anhydrous ethyl acetate and 20.2 g (0.2 mole) of triethylamine. A solution of 52.2 g (0.2 mole) of α-methyl-δ-iodovaleric acid chloride in 50 ml of ethyl acetate were added dropwise over the course of 50 minutes to this suspension at 20°C. After stirring for 4 hours at 20°C, the triethylammonium chloride formed was filtered off. The filtrate was freed from the solvent and the crystalline residue which remained was recrystallized from ligroin. This gave 35.1 g (47% of theory) of α-methyl-δ-iodovaleric acid N-(5-tert. -butyl-1,3,4-thiadiazol-2-yl)-amide of melting point 101.5°–102.5°C.

The ω-chlorocarboxylic acid amides listed in Table 2 which follows were prepared analogously:

Table 2

$$R-\underset{S}{\overset{N-N}{\underset{}{\bigvee}}}-NH-CO-\underset{CH_3}{\overset{}{C}}H-(CH_2)_n-CH_2Cl \quad (III)$$

| Example No. | R | n | Melting point [°C] |
|---|---|---|---|
| III | $CH_3$ | 1 | 139 – 140 |
| IV | $C_2H_5$ | 1 | 119 – 120 |
| V | $n-C_3H_7$ | 1 | 102 |
| VI | $i-C_3H_7$ | 1 | 83 – 84 |
| VII | $CF_3$ | 1 | 86 – 88 |
| VIII | $CH_3S$ | 1 | 77 – 79 |
| IX | $C_2H_5S$ | 1 | 54 |
| X | $CH_3SO_2$ | 1 | 108 |
| XI | $C_2H_5SO_2$ | 1 | 114 |
| XII | $CH_3O$ | 1 | 88 – 89 |

The active compounds of the formula (I) are distinguished by a high herbicidal potency. They can therefore be employed very successfully as weedkillers.

Weeds in the broadest sense are plants which grow in locations where they are not desired. The following may be mentioned as weeds: dicotyledons such as mustard (Sinapis), cress (Lepidium), cleavers (Galium), chickweed Stellarial, camomile (Matricaria), gallant soldier (Galinsoga), goosefoot (Chenopodium), annual nettle (Urtica) and groundsel (Senecio), and monocotyledons such as timothy (Phleum), blue grass (Poa), fescue (Festuca), goosegrass (Eleusine), foxtail grass (Setaria), ryegrass (Lolium) and barnyard grass (Echinochloa).

The active compounds according to the invention have a very great influence on plant growth, but in different ways so that they can be used as selective herbicides. In particular, they are suitable for combating grasses such as species of Echinochloa or Lolium. In addition, they are distinguished by a particularly good activity against weeds such as camomile (Matricaria), annual nettle (Urtica) and wild carrots (Daucus). When used in larger amounts (greater than 25 kg/ha) they can also be used as total herbicides.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene -fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention can be present in the formulations as a mixture with other active compounds, such as fungicides, insecticides and acaricides.

The formulations in general contain from 0.1 to 95 percent by weight of active compound, preferably from 0.5 to 90 percent by weight.

The active compounds can be used as such, in the form of their formulations or in the use forms prepared therefrom, such as ready-to-use solutions, emulsions, suspensions, powders, pastes and granules. They may be used in the customary manner, for example by spraying, atomizing, dusting, scattering, and watering.

They can be used both by the post-emergence process and by the pre-emergence process. When using the active compounds as total herbicides, they are preferably used after the emergence of the plants, whereas when used for the selective combating of weeds they are preferably used before emergence.

The amount of active compound employed can vary within wide ranges. It depends essentially on the nature of the desired effect. In general, the amounts used are between 0.1 and 25 kg/ha, preferably between 0.25 and 10 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier. The present invention further provides means of yielding crops protected from damage by weeds by being grown in areas in which immediately prior to and/or during the time of the growing a compound of the present invention was applied alone or in admixuture with a diluent or carrier. It will be seen that the usual methods of providing a harvested crop may be improved by the present invention.

The herbicidal activity of the active compounds according to the invention can be seen from the biotest Examples which follow:

Example A

Post-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. Depending on the concentration of the spray liquor, the amount of water used was between 1,000 and 2,000 l/na. After three weeks, the degree of damage to the plants was determined and characterized by the values 0–5, which have the following meaning:

0 no effect
1 a few slightly burnt spots
2 marked damage to leaves
3 some leaves and parts of stalks partially dead
4 plant partially destroyed 5 plant completely dead.

The active compounds, the amounts used and the results can be seen from the table which follows:

amount of water per unit area. The concentration of the active compound in the preparation was of no importance, only the amount of active compound applied Table A Post-emergence test

| Active compound | Amount of active compound used, kg/ha | Echino-chloa | Cheno-podium | Sina-pis | Galin-soga | Stell-aria | Urt-ica | Matri-caria | Dau-cus | Oats | Cot-ton | Wheat | Beans |
| --- | --- | --- | --- | --- | --- | --- | --- | --- | --- | --- | --- | --- | --- |
| [structure] (known) | 2.0 | 5 | 5 | 5 | 5 | 5 | 5 | 2 | 0 | 4 | 2 | 4 | 3 |
|  | 1.0 | 4–5 | 5 | 5 | 5 | 5 | 5 | 0 | 0 | 3 | 2 | 3 | 3 |
|  | 0.5 | 3 | 4 | 5 | 5 | 4 | 3 | 0 | 0 | 2 | 2 | 2 | 3 |
|  | 0.25 | 2 | 2 | 4–5 | 2 | 2 | 2 | 0 | 0 | 0 | 1 | 2 | 2 |
| [structure] (known) | 2.0 | 3–4 | 2 | 5 | 2–3 | 2 | 3 | 3 | 1 | 2 | 2 | 3 | 3 |
|  | 1.0 | 3 | 1 | 4–5 | 2 | 1 | 2 | 1 | 0 | 0 | 0 | 3 | 2 |
|  | 0.5 | 2 | 0 | 3 | 1 | 0 | 0 | 0 | 0 | 0 | 0 | 2 | 2 |
|  | 0.25 | 1 | 0 | 0 | 0 | 0 | 0 | 0 | 0 | 0 | 0 | 1 | 2 |
| [structure] (1) | 2.0 | 5 | 5 | 5 | 5 | 5 | 5 | 5 | 5 | 4–5 | 5 | 4–5 | 5 |
|  | 1.0 | 4–5 | 5 | 5 | 5 | 5 | 5 | 4 | 5 | 4 | 3 | 4 | 5 |
|  | 0.5 | 4 | 5 | 5 | 5 | 3 | 5 | 4 | 5 | 2 | 2 | 2–3 | 4–5 |
|  | 0.25 | 3 | 5 | 5 | 5 | 2–3 | 5 | 4 | 3 | 2 | 1 | 2 | 4 |
| [structure] (2) | 2.0 | 5 | 5 | 5 | 5 | 5 | 5 | 5 | 3 | 4–5 | 2 | 4 | 5 |
|  | 1.0 | 4–5 | 4–5 | 5 | 5 | 4 | 5 | 3 | 2 | 4 | 2 | 3 | 3 |
|  | 0.5 | 4 | 4–5 | 5 | 5 | 2 | 5 | 2 | 1 | 2 | 1 | 3 | 3 |
|  | 0.25 | 3 | 3 | 4 | 2 | 0 | 4 | 1 | 0 | 0 | 0 | 2 | 2 |

Example B

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the per unit area being decisive. After three weeks, the degree of damage to the test plants was determined and characterized by the values 0–5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The active compounds, the amounts applied and the results obtained can be seen from the following table:

Table B

Pre-emergence test

| Active compound | Amount of active compound used, kg/ha | Sina-pis | Echino-chloa | Cheno-podium | Lol-ium | Stell-aria | Galin-soga | Matri-caria | Oats | Cot-ton | Wheat | Buck-wheat | Maize |
| --- | --- | --- | --- | --- | --- | --- | --- | --- | --- | --- | --- | --- | --- |
| [structure] (known) | 10 | 4–5 | 3–4 | 5 | 3 | 4–5 | 5 | 5 | 4 | 2 | 1 | 2 | 2 |
|  | 5 | 4–5 | 3 | 4 | 1 | 4–5 | 5 | 5 | 3 | 2 | 0 | 1 | 2 |
|  | 2.5 | 3 | 3 | 4 | 0 | 4 | 5 | 4 | 2 | 0 | 0 | 0 | 0 |
|  | 1.25 | 3 | 1 | 2 | 0 | 3 | 4–5 | 3–4 | 2 | 0 | 0 | 0 | 0 |
| [structure] | 10 | 4 | 4 | 3 | 3 | 4 | 4–5 | 4–5 | 2 | 2 | 2 | 0 | 2 |
|  | 5 | 3 | 3 | 2 | 2 | 3 | 4 | 4 | 2 | 1 | 1 | 0 | 0 |
|  | 2.5 | 3 | 2 | 2 | 2 | 3 | 3 | 3 | 1 | 0 | 0 | 0 | 0 |
|  | 1.25 | 2 | 2 | 2 | 2 | 2 | 2 | 1 | 0 | 0 | 0 | 0 | 0 |

Table B-continued

Pre-emergence test

| Active compound | Amount of active compound used, kg/ha | Sina-pis | Echino-chloa | Cheno-podium | Lol-ium | Stell-aria | Galin-soga | Matri-caria | Oats | Cot-ton | Wheat | Buck-wheat | Maize |
|---|---|---|---|---|---|---|---|---|---|---|---|---|---|
| (known) 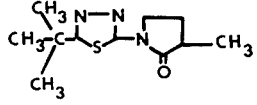 (1) | 10 | 5 | 5 | 5 | 4 | 5 | 5 | 5 | 4–5 | 4 | 4 | 4–5 | 4 |
|  | 5 | 5 | 4–5 | 5 | 3 | 5 | 5 | 5 | 4 | 3 | 3 | 4–5 | 3 |
|  | 2.5 | 5 | 4 | 5 | 3 | 5 | 5 | 5 | 4 | 3 | 2 | 3 | 2 |
|  | 1.25 | 4–5 | 3 | 5 | 1 | 4 | 5 | 5 | 3 | 2 | 2 | 2 | 1 |
| 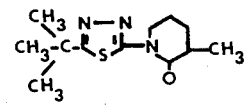 (2) | 10 | 4 | 5 | 5 | 4 | 5 | 5 | 5 | 4 | 3 | 3 | 2 | 3 |
|  | 5 | 4 | 5 | 5 | 3 | 5 | 5 | 5 | 3 | 2 | 2 | 1 | 2 |
|  | 2.5 | 3 | 4–5 | 5 | 3 | 4–5 | 4–5 | 5 | 3 | 2 | 1 | 0 | 2 |
|  | 1.25 | 2 | 3 | 4 | 2 | 4 | 4 | 4–5 | 2 | 2 | 0 | 0 | 1 |

It will be appreciated that the instant specification and examples are set forth by way of illustration and not limitation, and that various modifications and changes may be made without departing from the spirit and scope of the present invention.

What is claimed is:

1. Cyclic N-thiadiazolyl-(2)-carboxylic acid amide compounds of the formula:

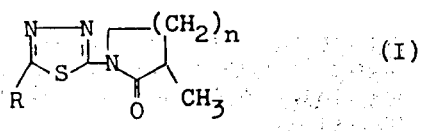

wherein
R is alkyl, haloalkyl, alkylthio, alkylsulfonyl or alkoxy, and contains not more than 5 carbon atoms and
n is 1 or 2.

2. Cyclic N-thiadiazolyl-(2)-carboxylic acid amide compounds as claimed in claim 1 wherein R is alkyl of up to 5 carbon atoms.

3. Cyclic N-thiadiazolyl-(2)-carboxylic acid amide compounds as claimed in claim 1 wherein R is haloalkyl of up to 5 carbon atoms and up to 5 halogen atoms.

4. Cyclic N-thiadiazolyl-(2)-carboxylic acid amide compounds as claimed in claim 1 wherein R is alkylthio of up to 4 carbon atoms.

5. Cyclic N-thiadiazolyl-(2)-carboxylic acid amide compounds as claimed in claim 1 wherein R is alkylsulfonyl of up to 4 carbon atoms.

6. Cyclic N-thiadiazolyl-(2)-carboxylic acid amide compounds as claimed in claim 1 wherein R is alkoxy of up to 4 carbon atoms.

7. Cyclic N-thiadiazolyl-(2)-carboxylic acid amide compounds as claimed in claim 1 wherein n is 1.

8. Cyclic N-thiadiazolyl-(2)-carboxylic acid amide compounds as claimed in claim 1 wherein n is 2.

9. Cyclic N-thiadiazolyl-(2)-carboxylic acid amide compound designated 1-[5-tert.-butyl-1,3,4-thiadiazolyl-(2)]-3-methyl-2-pyrrolidone.

10. Cyclic N-thiadiazolyl-(2)-carboxylic acid amide compound designated 1-[5-tert.-butyl-1,3,4-thiadiazolyl-(2)]-3-methyl-2-piperidone.

11. Herbicidal composition comprising an agriculturally acceptable carrier and, in effective amounts, a cyclic N-thiadiazolyl-(2)-carboxylic acid amide compound as claimed in claim 1.

12. Method of combating undesired vegetation, which method comprises applying to such vegetation or its habitat herbicidally effective amounts of a cyclic N-thiadiazolyl-(2)-carboxylic acid amide compound of the formula:

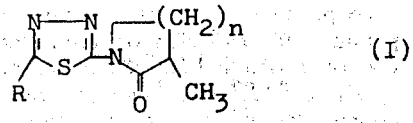

wherein
R is alkyl, haloalkyl, alkylthio, alkylsulfonyl or alkoxy, and
n is 1 or 2.

13. Method as claimed in claim 12 wherein said compound is at least one of:
1-[5-tert.-butyl-1,3,4-thiadiazolyl-(2)]-3-methyl-2-pyrrolidone
and
1-[5-tert.-butyl-1,3,4-thiadiazolyl-(2)]-3-methyl-2-piperidone 14. Method as claimed in claim 12 wherein said compound is applied in an amount of from 0.1 to 25 kg per hectare.

* * * * *